United States Patent
Ruiter et al.

(10) Patent No.: US 11,877,892 B2
(45) Date of Patent: Jan. 23, 2024

(54) DEVICE AND METHOD FOR 3D ULTRASOUND-BASED REFLECTION AND TRANSMISSION TOMOGRAPHY OF A BODY

(71) Applicant: Karlsruher Institut für Technologie, Karlsruhe (DE)

(72) Inventors: Nicole Ruiter, Durmersheim (DE); Hartmut Gemmeke, Stutensee (DE); Michael Zapf, Karlsruhe (DE); Torsten Hopp, Speyer (DE); Nima Rashvand, Karlsruhe (DE)

(73) Assignee: Karlsruher Institut für Technologie, Karlsruhe (DE)

( * ) Notice: Subject to any disclaimer, the term of this patent is extended or adjusted under 35 U.S.C. 154(b) by 0 days.

(21) Appl. No.: 17/924,109

(22) PCT Filed: May 6, 2021

(86) PCT No.: PCT/EP2021/062003
§ 371 (c)(1),
(2) Date: Nov. 8, 2022

(87) PCT Pub. No.: WO2021/224398
PCT Pub. Date: Nov. 11, 2021

(65) Prior Publication Data
US 2023/0218274 A1 Jul. 13, 2023

(30) Foreign Application Priority Data

May 8, 2020 (EP) ..................................... 20173617

(51) Int. Cl.
*A61B 8/00* (2006.01)
*A61B 8/08* (2006.01)
(Continued)

(52) U.S. Cl.
CPC .......... *A61B 8/4494* (2013.01); *A61B 8/0825* (2013.01); *A61B 8/14* (2013.01);
(Continued)

(58) Field of Classification Search
CPC .............................. A61B 8/406; A61B 8/0825
See application file for complete search history.

(56) References Cited

U.S. PATENT DOCUMENTS 7,264,592 B2    9/2007   Shehada
10,123,770 B2  11/2018  Szpak et al.
(Continued)

FOREIGN PATENT DOCUMENTS

EP    0105812 A1 *  4/1984   ........... A61B 8/0825
EP    0105812 A1    4/1984
(Continued)

OTHER PUBLICATIONS

International Search and Written Opinion for PCT/EP2021/062003 dated Jul. 9, 2021.
(Continued)

*Primary Examiner* — Joel Lamprecht
*Assistant Examiner* — Nyrobi Celestine
(74) *Attorney, Agent, or Firm* — Thomas Horstemeyer, LLP

(57) ABSTRACT

A device is provided for ultrasound-based reflection and transmission tomography. A plurality of ultrasonic transducers are held around an imaging volume to be filled with an ultrasonic coupling medium, the transducer holder having an opening for inserting, into the imaging volume, at least one part of a body to be imaged. During imaging, the body to be imaged is supported, where a support-member-opening allows access to the transducer holder by at least one part of the body. A diaphragm is arranged across the support-member-opening such that a center of a diaphragm-opening
(Continued)

is placed substantially at a predetermined position. The ultrasonic coupling medium flows out of the imaging volume when at least one part of the body to be imaged is inserted into the imaging volume filled with the ultrasonic coupling medium and/or during imaging.

17 Claims, 9 Drawing Sheets

(51) Int. Cl.
*A61B 8/14* (2006.01)
*A61B 8/15* (2006.01)

(52) U.S. Cl.
CPC ............... *A61B 8/15* (2013.01); *A61B 8/406* (2013.01); *A61B 8/4209* (2013.01); *A61B 8/483* (2013.01)

(56) References Cited

U.S. PATENT DOCUMENTS

| | | | |
|---|---|---|---|
| 11,064,974 | B2 | 7/2021 | Szpak et al. |
| 2004/0064046 | A1 | 4/2004 | Shehada |
| 2014/0276068 | A1 | 9/2014 | Szpak et al. |
| 2017/0273660 | A1* | 9/2017 | Chang .................... A61B 8/406 |
| 2019/0038255 | A1 | 2/2019 | Szpak et al. |

FOREIGN PATENT DOCUMENTS

| | | | |
|---|---|---|---|
| EP | 2253274 A1 * | 11/2010 | ........... A61B 8/0825 |
| EP | 2253274 A1 | 11/2010 | |
| KR | 20130080196 A * | 7/2013 | ........... A61B 8/0825 |

OTHER PUBLICATIONS

Extended European Search Report for European Application No. 20 173 617.0 dated Oct. 20, 2020.
International Preliminary Report on Patentability for PCT/EP2021/062003 dated Nov. 8, 2022.

* cited by examiner

DEVICE AND METHOD FOR 3D ULTRASOUND-BASED REFLECTION AND TRANSMISSION TOMOGRAPHY OF A BODY

CROSS-REFERENCE TO RELATED APPLICATIONS

This application is a 35 U.S.C. § 371 National Stage Patent Application of, and claims priority to, Patent Cooperation Treaty Application number PCT/EP2021/062003, filed on 6 May 2021, entitled "DEVICE AND METHOD FOR 3D ULTRASOUND-BASED REFLECTION AND TRANSMISSION TOMOGRAPHY," which claims priority to and the benefit of EP Patent Application number 20173617.0 filed on 8 May 2020, where both of these applications are incorporated herein by reference in their entirety.

The application relates to a device for ultrasound-based reflection and transmission tomography as well as to a method for imaging at least one part of a body with ultrasound-based reflection and transmission tomography.

BACKGROUND

Systems for ultrasound computer tomography (USCT) can image an object, e.g. a part of a body, using ultrasound waves for imaging.

For example, EP 3107459 B1 discloses a device for ultrasound-based reflection and transmission tomography, the device including a measurement volume filled with an ultrasonic coupling medium and having an opening for inserting a body to be examined and a lateral surface remote from the opening, and a number of ultrasonic transducers arranged remotely from the opening of the measurement volume, arranged in direct contact with the ultrasonic coupling medium, and arranged oriented into the measurement volume. The arrangement of the ultrasonic transducers around the measurement volume aperiodically follows a random uniform distribution.

SUMMARY

Especially the 3D sound speed and attenuation distribution measured by transmission tomography in biological matter may allow identifying different tissue types. Furthermore, the 3D sound speed distribution may allow correcting the reflection tomography to a more exact result than in standard sonography.

According to an aspect, the problem relates to facilitating imaging by 3D ultrasound computer tomography with improved image quality.

This problem is solved by the features disclosed by the independent claims. Further exemplary embodiments are defined by the dependent claims.

According to an aspect, a device for ultrasound-based reflection and transmission tomography is provided. The device comprises:
- a transducer holder configured to hold a plurality of ultrasonic transducers around an imaging volume to be filled with an ultrasonic coupling medium, the transducer holder having an opening for inserting, into the imaging volume, at least one part of a body to be imaged, wherein the transducer holder is configured to move, during imaging of the at least one part of the body to be imaged, with respect to the body to be imaged;
- a support member configured to support, during imaging, the body to be imaged, the support member having a support-member-opening allowing access to the transducer holder by the at least one part of the body to be imaged;
- a diaphragm having a diaphragm-opening, the diaphragm being arranged across the support-member-opening such that a center of the diaphragm-opening is placed substantially at a predetermined position, wherein the diaphragm comprises a material that has a higher transmissivity of ultrasound than a material of the support member;
- an outlet for the ultrasonic coupling medium to flow out of the imaging volume when the at least one part of the body to be imaged is inserted into the imaging volume filled with the ultrasonic coupling medium and/or during imaging; and
- an elastic membrane comprising a fluid-tight material connecting the transducer holder and the outlet in order to guide the ultrasonic coupling medium flowing out of the imaging volume towards the outlet.

In the present disclosure, the "imaging volume" may be defined by an inner surface of the transducer holder.

In the present disclosure, the "body to be imaged" may be a human body.

In some circumstances, however, the "body to be imaged" may be a technical structure that requires a non-destructive testing (e.g., for structural and/or defect analysis). In other words, the present disclosure may also be applied to structural and/or defect analysis of a technical structure.

With the device according to the above-stated aspect and various embodiments thereof, an image of the at least one part of the body inserted into the imaging volume may be obtained. The image itself does not provide any diagnosis. Rather, the image may be subsequently analyzed. Such an analysis may provide for e.g. medical diagnosis.

In particular, in some circumstances, the "one part of the body to be imaged" may be a human breast (particularly, a female breast). In case the "one part of the body to be imaged" is a human breast, images obtained by various aspects and/or exemplary embodiments described herein may be subsequently used for diagnosis of breast cancer, for example.

The device according to the above stated aspect may provide a "3D ultrasound computer tomography" (3D USCT). 3D may mean an unfocussed data-accumulation (e.g., different type of sensors—unfocussed) where the reconstruction can deliver the focusing. That may be considered fundamentally different from 2D or "2.5D" tomography, which uses focused data-accumulation and transducers as well as interpolation of 2D images from 2D measurements to obtain a 3D image. 3D USCT has been developed at the Institute for Process Data Processing and Electronics (IPE) of the Karlsruhe Institute of Technology (KIT). 3D USCT can be considered as an innovative imaging system for improving early detection of breast cancer, which may allow early diagnosis and thus a higher survival probability.

3D USCT may enable three-dimensional imaging of the breast with high resolution in the sub-millimeter range. The method may promise high sensitivity and specificity. An objective may be detection of tumors with a size below 5 mm and thus significantly earlier than with other screening procedures used today. By the use of ultrasound, the patient is not exposed to ionizing radiation, in contrast to the standard X-ray mammography examination. The examination is painless and can potentially be carried out in a very cost-effective manner.

The imaging principle of the 3D USCT may be based on several thousand ultrasound transducers (e.g., transmitter and receiver) that enclose the breast in an imaging volume filled with an ultrasonic coupling medium (e.g. water bath). During an examination, the patient may lie on his/her stomach on a patient support and bring one breast into the imaging volume. The ultrasonic transducers may be rotated and/or lifted around the breast immersed in the ultrasonic coupling medium during the recording process (in other words, during imaging).

Accordingly, in some exemplary embodiments, the transducer holder may be configured to hold more than 1000 ultrasonic transducers. In some circumstances, the number of ultrasonic transducers to be held by the transducer holder may exceed 2000 and up to 10000. In some preferred exemplary embodiments, the number of ultrasonic transducers may be 5000, 3000 or 2000. Specifically in a particular exemplary embodiment, the transducer holder may be configured to hold 2304 transducers.

In the present disclosure, the "ultrasonic coupling medium" may be a liquid such as water or aqueous solution. Alternatively, the ultrasonic coupling medium may be an ultrasonic coupling gel, an ultrasonic coupling oil, or formalin etc. Formalin may be used, for example, in case of imaging cadavers.

In the device according to the above-stated aspect and various embodiments thereof, the diaphragm may be fixed in its position to the support member.

In some exemplary embodiments, the elastic membrane may be made of silicon.

In the device according to the above-stated aspect and various embodiments thereof, the predetermined position may be a center of an opening of the transducer holder. This may facilitate centering the at least one part of the body on the device. Even when the predetermined position is out of the center of the opening of the transducer holder, however, if necessary, the resulting images may be reconstructed as if the predetermined position was indeed the center of the opening of the transducer holder. Accordingly, in some exemplary embodiments, the predetermined position may be a center of an opening of the transducer holder to obtain an optimal resolution and/or contrast at imaging of the at least one part of the body to be imaged.

Further, in the device according to the above-stated aspect, the elastic membrane can connect the transducer holder and the outlet in order to guide the ultrasonic coupling medium flowing out of the imaging volume towards the outlet, whilst the ultrasonic coupling medium is kept at a constant level during imaging with respect to the at least one part of the body to be imaged.

With regards to keeping the level of the ultrasonic coupling medium constant with respect to the at least one part of the body to be imaged, the device according to the above-stated aspect may further comprise a fixing member that is configured to fix the elastic membrane to the outlet and that is configured to keep, during imaging, a level of the ultrasonic coupling medium constant relative to the at least one part of the body to be imaged. This configuration may enable keeping the at least one part of the body to be imaged immersed in the ultrasonic coupling medium in the same manner throughout the imaging process, even when, for example, the transducer holder moves during imaging with respect to the at least one part of the body to be imaged. This may contribute to capturing a complete 3D image of the at least one part of the body to be imaged.

The device according to the above-stated aspect can facilitate imaging by ultrasound computer tomography with improved image quality.

In case of imaging a human breast with USCT, rotation and lifting mechanism of ultrasonic transducers for the imaging can be realized in a waterproof manner by a conventional telescope mechanism, for example. The device according to the above-stated aspect can carry out the imaging in a more reliable manner with a simpler and/or smaller configuration than such a conventional telescope mechanism.

For example, in the device according to the above-stated aspect, since the elastic membrane comprising the fluid-tight material connecting the transducer holder and the outlet is provided in order to guide the ultrasonic coupling medium flowing out of the imaging volume towards the outlet, the ultrasonic transducers can move as the transducer holder moves during imaging while being protected from the ultrasonic coupling medium by the fluid-tight material of the elastic membrane. Further, with the elastic membrane guiding the ultrasonic coupling medium towards the outlet from the imaging volume, the ultrasonic coupling medium displaced by the at least one part of the body inserted into the imaging volume can be drained in a defined manner. Further, for example, the elastic membrane can reduce motion resistance for the transducer holder, thereby reducing sudden jerky movement and resulting positional inaccuracies during imaging. Furthermore, the fixing member configured to fix the elastic membrane to the outlet can keep the level of the ultrasonic coupling medium constant at the at least one part of the body to be imaged, when, for example, the transducer holder is lifted towards the body to be imaged.

Further, for example, in the device according to the above-stated aspect, the diaphragm having the diaphragm-opening may facilitate centering of the at least one part of the body in the imaging volume while preventing one or more undesired parts of the body (in other words, parts of the body other than the part(s) to be imaged) from penetrating the imaging volume.

In some exemplary embodiments, the diaphragm may be fixed at a bottom of the support member such that the center of the diaphragm-opening is placed substantially at the center of the opening of the transducer holder. Such an arrangement of the diaphragm may further facilitate centering the at least one part of the body to be imaged in the imaging volume.

Further, in some exemplary embodiments, the diaphragm may be arranged on top of the support member such that the center of the diaphragm-opening is placed substantially at the center of the opening of the transducer holder. In such exemplary embodiments, in case of imaging a human breast, a larger distance may be provided between the breast cleavage and the transducer holder than with other exemplary embodiments in which the diaphragm is fixed at the bottom of the support member.

Further, the material of the diaphragm may be selected such that its reflectivity and attenuation for ultrasound is minimal in order not to interfere with the imaging process so that part(s) of the body covered by the diaphragm may also be imaged. In other words, the material of the diaphragm may be selected to be transparent to ultrasonic waves.

Further, in some exemplary embodiments, the diaphragm may comprise a textile made of a material selected such that its reflectivity and attenuation for ultrasound is minimal in order not to interfere with the imaging process. Employing a textile for the diaphragm may provide flexible support for the at least one part of the body to be imaged while preventing one or more parts of the body other than the part of interest for the imaging from entering into the imaging volume.

In the device according to any one of the above-stated aspect and various embodiments thereof, the diaphragm may be made of the material that has the higher transmissivity of ultrasound than the material of the support member.

In some exemplary embodiments, the material of the transducer holder and the support member may be polyoxymethylene (POM), polyether ether ketone (PEEK) and/or polycarbonate (PC), for example.

Further, in the device according to any one of the above-stated aspect and various embodiments thereof, the elastic membrane may be configured to allow the transducer holder to move while preventing the ultrasonic coupling medium outside the imaging volume from coming into contact with the plurality of ultrasonic transducers. This may prevent electronic components of the plurality of ultrasonic transducers (e.g., exposed at an outer side of the transducer holder, the outer side being a side opposite to a side defining the imaging volume) from being damaged by the ultrasonic coupling medium. Further, for example, risk of short circuit faults of cabling of the transducer(s) can be reduced with this configuration.

In the device according to any one of the above-stated aspect and various embodiments thereof, the transducer holder may be configured to rotate, during imaging of the at least one part of the body to be imaged, with respect to the body to be imaged. In some circumstances, an axis of rotation of the transducer holder may be substantially perpendicular to the opening of the transducer holder.

Further, in the device according to any one of the above-stated aspect and various embodiments thereof, the transducer holder may be configured to move, during imaging of the at least one part of the body to be imaged, in a direction substantially perpendicular to the opening of the transducer holder. In other words, the transducer holder may be lifted towards (and/or lowered to be away from) the support member.

In the device according to any one of the above-stated aspect and various embodiments thereof, a distance from an upper transducer to a lower edge of the support-member-opening may be up to 3 mm when the transducer holder is placed in a position closest to the support member during movement of the transducer holder and particularly when the diaphragm (12) sags towards the transducer holder (14). In some circumstances, the distance from the upper transducer to the lower edge of the support-member-opening may be up to 8 mm when the transducer holder is placed in the position closest to the support member during movement of the transducer holder. The upper transducer may be one of the plurality of ultrasonic transducers that is held closest, among the plurality of ultrasonic transducers, to the opening of the transducer holder. The lower edge may be an edge of the support-member-opening on a side facing the transducer holder. Particularly in case of imaging a human breast, such a small distance from the upper transducer to the lower edge of the support-member-opening and/or the diaphragm transparent to ultrasonic waves as mentioned above may enable imaging not only of the breast but also of one or more parts of the breast base (e.g., chest). This may be advantageous for later diagnosis. For example, particularly for breast cancer examination, imaging of not only the breast but also the breast base may be desirable. In order to image the breast base, it may be preferable that the top transducers (e.g., ultrasonic transducers located the closest to the breast base) come as close as possible to the chest in the maximum translation. Further, enabling imaging of one or more parts of the chest in addition to the breast may be advantageous in case of imaging a male breast and/or of imaging tissue in the environment of the breast.

As also stated above, in case of imaging a human breast with USCT, rotation and lifting mechanism of ultrasonic transducers for the imaging can be realized in a waterproof manner by a conventional telescope mechanism, for example. According to experiments carried out by the inventors, however, the waterproof telescope solution resulted in a loss of more than 3 cm of the imaging area when it was directly coupled to the chest. In contrast, with the above-stated device in which the distance from the upper transducer to the lower edge of the support-member-opening is up to 3 mm, such a loss of the imaging area with the conventional telescope mechanism can be avoided or reduced.

Further in the device according to any one of the above-stated aspect and various embodiments thereof, the diaphragm may be placed at the lower edge of the support-member-opening. This may further facilitate imaging of one or more parts of the chest in addition to the breast, for example.

Further, placing the diaphragm at the lower edge of the support-member-opening may facilitate positioning the at least one part of the body in a desired position with respect to the level of ultrasonic coupling medium and, thus, for imaging.

In some exemplary embodiments, the diaphragm may be placed on top of the support member across the support-member-opening such that a center of the diaphragm-opening is placed substantially at a center of the opening of the transducer holder. Such a configuration may make the structure of the device simpler and/or may enable a faster exchange of the diaphragm. Further, with such a configuration, a simpler and/or more cost-effective support member may be employed for the device. Moreover, such a configuration can also facilitate correct positioning of the at least one part of the body in the center of the support-member-opening.

In the device where the diaphragm is placed on top of the support member, the support member may comprise a groove around the support-member-opening and the diaphragm may be attached to at least one diaphragm support that is configured to fit in the groove. The diaphragm may then be placed on top of the support member across the support-member-opening by fitting the at least one diaphragm support in the groove. The diaphragm may be attached to the at least one diaphragm support with a glue and/or with one or more screws. In some exemplary embodiments, the at least one diaphragm support may be a clamp ring. In some exemplary embodiments, the at least one diaphragm support may be a pair of clamp rings and the diaphragm may be tightly held between the pair of clamp rings.

Further, in the device according to any one of the above-stated aspect and various embodiments thereof, the diaphragm may be exchangeable for adapting to different sizes of the at least one part of the body to be imaged. Such exchangeable diaphragms can, for example, in case of imaging human breasts, automatically center breasts of different sizes in the imaging volume. Further, with exchangeable diaphragms, hygienic safety can increase. For example, removing the diaphragm for exchange may make it easier to clean other parts of the device, e.g., the support member, the transducer holder, the elastic membrane, etc.

Further, in the device according to any one of the above-stated aspect and various embodiments thereof, the material of the diaphragm may be hemp. According to experiments carried out by the inventors, hemp (in particular, wet hemp) was found to be a very weakly ultrasound reflecting and absorbing textile. Further, because of its high strength (e.g., compared to cotton or wool), hemp may be considered as being particularly suitable for keeping parts of the body other than the part(s) of interest for imaging away from the imaging volume. Moreover, employing hemp for the diaphragm may facilitate the diaphragm to bend below the lower edge of the support-member-opening, thereby facilitating imaging not only a breast but also one or more parts of a chest, in case of imaging a human breast. This may be advantageous for an imaging algorithm that can reconstruct also tissue structures above the line of sight of the transducers (in other words, out of plane).

Further, in the device according to any one of the above-stated aspect and various embodiments thereof, the support-member-opening may correspond to the opening of the transducer holder. Particularly in some circumstances, the support-member-opening may be smaller than the opening of the transducer holder.

According to another aspect, a method is provided for imaging at least one part of a body with ultrasound-based reflection and transmission tomography. The method comprises:

providing the device according to any one of the above-stated aspect and various embodiments thereof;
providing the plurality of ultrasonic transducers on the transducer holder;
filling the imaging volume with the ultrasonic coupling medium;
inserting the at least one part of the body into the imaging volume; and
imaging the at least one part of the body by moving the transducer holder with respect to the body to be imaged.

In the method according to the above-stated aspect, the transducer holder may be rotated, during the imaging, with respect to the body to be imaged. An axis for the rotation may be substantially perpendicular to the opening of the transducer holder. Additionally or alternatively, the transducer holder may be moved, during the imaging, in a direction substantially perpendicular to the opening of the transducer holder. The movement may be used to cover a full surface (or almost full surface) of the at least part of the body to be imaged with ultrasound to achieve higher resolution and/or contrast.

An image of the at least one part of the body obtained by the method according to the above-stated aspect may subsequently be analyzed for e.g., medical diagnosis.

Any one of the above-stated aspects and various embodiments described herein may achieve one or more of the following technical effects:

allowing, during imaging, movement of the plurality of ultrasonic transducer held by the transducer holder while protecting the plurality of ultrasonic transducer from the ultrasonic coupling medium, thereby facilitating imaging;
reducing motion resistance for the transducer holder, thereby reducing sudden jerky movement and resulting positional inaccuracies during imaging;
enabling the ultrasonic coupling medium to drain out from the imaging volume in a defined manner and keeping a level of the ultrasonic coupling medium constant with respect to the at least one part of the body to be imaged, when the at least one part of the body to be imaged is inserted into the imaging volume and/or during imaging (e.g., when the transducer holder is lifted towards the support member);
enabling imaging of a desired part of the body, e.g., in case of imaging a human breast, enabling imaging of a breast base as well as the breast;
facilitating centering of the at least one part of the body in the imaging volume;
facilitating preventing one or more undesired parts of the body (in other words, parts of the body other than the part(s) to be imaged) from penetrating the imaging volume.

BRIEF DESCRIPTION OF THE DRAWINGS

Details of one or more implementations are set forth in the exemplary drawings and description below. Other features will be apparent from the description, the drawings, and from the claims. It should be understood, however, that even though embodiments are separately described, single features of different embodiments may be combined to further embodiments.

DETAILED DESCRIPTION OF EMBODIMENTS

In the following text, a detailed description of examples will be given with reference to the drawings. It should be understood that various modifications to the examples may be made. In particular, one or more elements of one example may be combined and used in other examples to form new examples.

In the following, exemplary embodiments of the present disclosure will be described with respect to a case where a human breast is imaged as the at least one part of the body using a device according to any one of the exemplary embodiments. It should be understood, however, the device according to any one of the aspects and various embodiments described herein may also be applied for imaging one or more parts of a body other than a human breast, for example, one or more parts of a human body other than a breast, or one or more parts of a body of a technical structure (e.g., mechanical pieces) in case of non-destructive testing.

Every year, over 1.6 million women worldwide fall ill with breast cancer. About 500,000 women die of the disease every year. This makes the mamma carcinoma the most common malignant tumor in women. A device according to the present disclosure may provide an innovative imaging method for improving early detection of breast cancer, which may allow early diagnosis and thus a higher survival probability.

Figure 1:
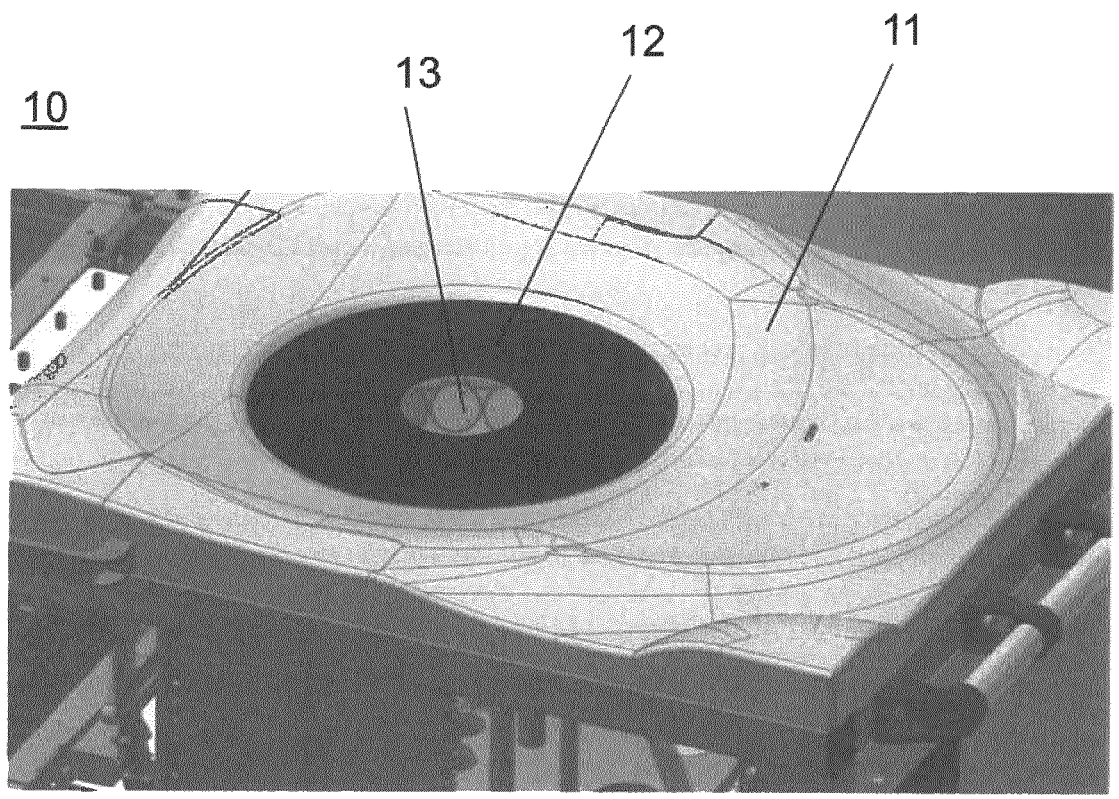
FIG. 1 shows a top view of a 3D USCT device according to an exemplary embodiment.

FIG. 1 shows a top view of a device according to an exemplary embodiment. A device 10 shown in FIG. 1 may be a 3D USCT system. As can be seen from FIG. 1, the device 10 may comprise a patient support 11 and a diaphragm 12 with a diaphragm-opening 13 (for e.g., a human breast).

The patient support 11 may support a patient during imaging with the device 10. The patient support 11 may be made of POM. The patient support may be considered as an example of a "support member" in the present disclosure and may have an opening allowing access to a transducer holder (not shown in FIG. 1) by at least one part of a body (e.g., a human breast) to be imaged.

Figure 2:
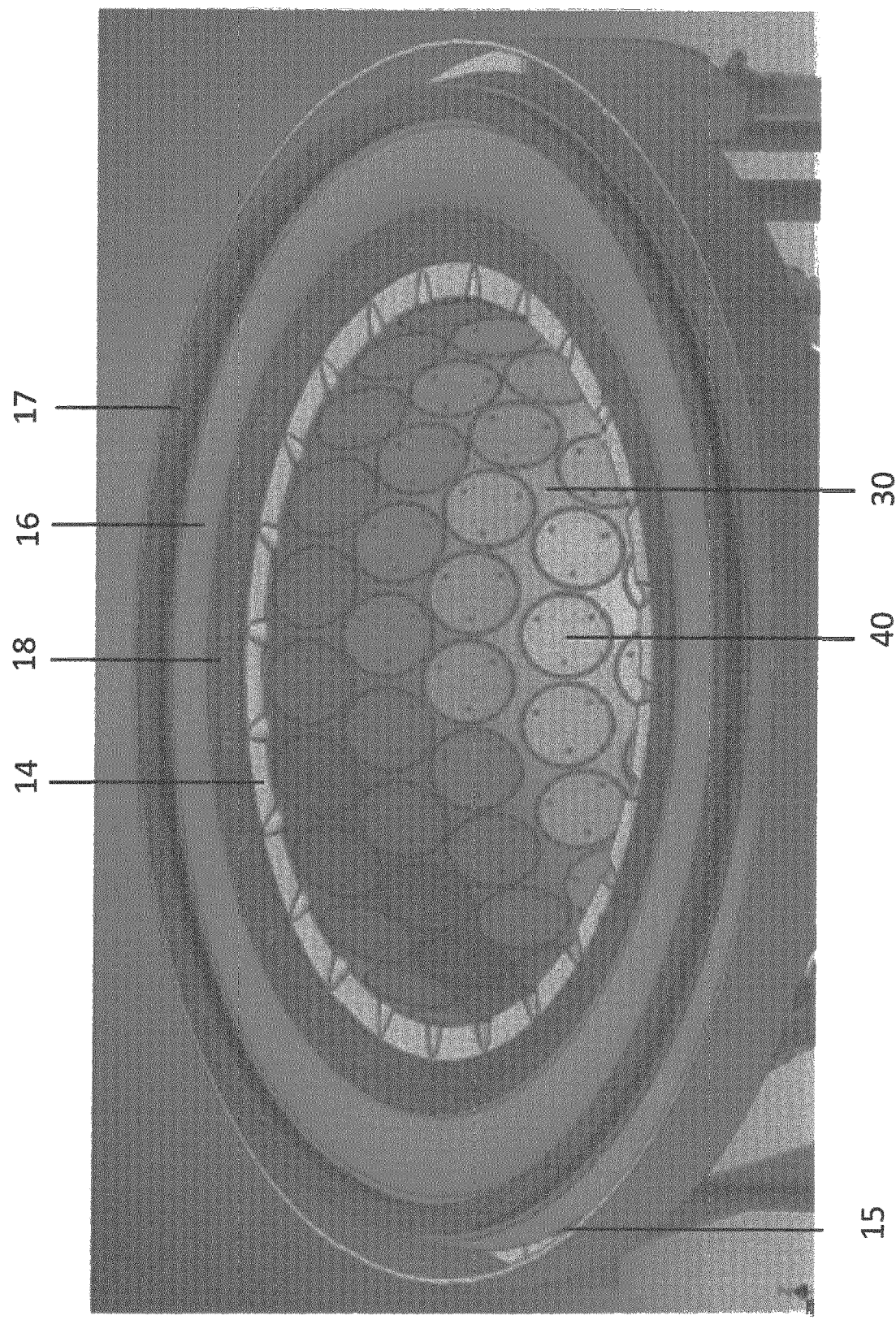
FIG. 2 shows a transducer holder and a water outlet comprised in the device shown in FIG. 1.

The diaphragm 12 having the diaphragm-opening 13 may be arranged across the opening of the patient support 11 such that a center of the diaphragm-opening 13 is placed substantially at a center of an opening of the transducer holder 14 (as shown in FIG. 2 which will be described later below). The at least one part of a body to be imaged may be inserted into the diaphragm-opening 13 to access the transducer holder 14. Placing the center of the diaphragm-opening 13 substantially at the center of the opening of the transducer holder 14 may facilitate centering the at least one part of the body to be imaged.

In some exemplary embodiments, the diaphragm 12 may be provided below a lower edge of the opening of the patient support 11. The lower edge of the opening of the patient support 11 may be an edge of the opening of the patient support 11 on a side facing the transducer holder. Further, the diaphragm 12 may bend below the lower edge of the opening of the patient support 11, in other words, bend towards the transducer holder 14 away from the patient support 11, as the at least one part of the body is inserted into the diaphragm-opening 13. Providing the diaphragm 12 below the lower edge of the opening of the patient support 11 and/or allowing the diaphragm 12 to bend below the lower edge of the patient support 11 may facilitate, for example, imaging not only a breast but also one or more parts of a chest, in case of imaging a breast. An image including both the breast and the breast base on the chest may be advantageous for later diagnosis.

The diaphragm 12 may comprise a textile made of a material that has a higher transmissivity for ultrasound than a material of the patient support 11. The textile may provide flexible support for the breast while preventing one or more parts of the body other than the part of interest for the imaging from accessing the transducer holder 14. In some exemplary embodiments, the diaphragm 12 may comprise a hemp textile which was found to be a very weakly ultrasound reflecting and absorbing textile. Further, because of its high strength, hemp may be considered as being particularly suitable for keeping parts of the body other than the part(s) of interest for imaging away from the imaging volume. Moreover, employing a hemp textile for the diaphragm 12 may further facilitate the diaphragm 12 to bend below the lower edge of the opening of the patient support 11 as stated above, thereby facilitating imaging not only a breast but also one or more parts of a chest, in case of imaging a breast.

FIG. 2 shows a transducer holder 14, a water outlet 15, an elastic membrane 16 and mounting rings 17 and 18 comprised in the device 10 shown in FIG. 1. FIG. 2 may be considered as a top view of the device 10 shown in FIG. 1 when the patient support 11 and the diaphragm 12 are removed from the device 10.

Referring to FIG. 2, the transducer holder 14 may be configured to hold a plurality of ultrasonic transducer arrays 40 (front views of which are shown in FIG. 2) around an imaging volume 30 to be filled with an ultrasonic coupling medium. In this particular example, the ultrasonic coupling medium is water. It should be noted, however, an ultrasonic coupling medium other than water may also be adopted for the device 10 in some other examples. A surface of the transducer holder 14, together with the surfaces of transducer arrays 40 and/or other component(s), may define a surface of the imaging volume 30 and the transducer holder 14 may have an opening for inserting, into the imaging volume, at least one part of a body (e.g., human breast) to be imaged. The transducer holder 14 may be configured to move, during imaging, with respect to the body to be imaged. Along with the movement of the transducer holder 14, the plurality of transducer arrays 40 held by the transducer holder 14 may move, during imaging, with respect to the body to be imaged. The details of the movement of the transducer holder 14 will be described later below.

The water outlet 15 may be provided for the water to flow out of the imaging volume when the at least one part of the body (e.g., human breast) to be imaged is inserted into the imaging volume filled with the water and/or during imaging. Specifically, for example, when the imaging volume is moved towards the body as the transducer holder 14 is moved during imaging, the at least one part of the body may be immersed in the water and displace the water. The displaced water can flow into the water outlet 15 without being spilt out of or inside into the device 10.

Further, the transducer holder 14 and the water outlet 15 may be connected by the elastic membrane 16 comprising a fluid-tight (e.g., watertight) material in order to guide the water flowing out of the imaging volume towards the water outlet 15. The elastic membrane 16 may be made of silicon. The elastic membrane 16 may be fixed to the transducer holder 14 and to the water outlet 15 by the mounting rings 17 and 18. Further details of the elastic membrane 16 will be described later below with reference to FIGS. 4, 5, 6a and 6b.

As mentioned above, the imaging principle of 3D USCT in the exemplary embodiment may also be based on several thousand ultrasonic transducers (e.g., transmitters and receivers, or transducers having both functions of a transmitter and a receiver) that enclose the human breast in the imaging volume (e.g. a water bath) defined by the transducer holder 14. In some examples, the number of the ultrasonic transducers employed may be more than 1000. In some preferred examples, the number of the ultrasonic transducers may exceed 2000 and up to 10000. In further preferred examples, the number of ultrasonic transducers may be 5000, 3000 or 2000. During imaging, the patient may lie on his/her stomach on the patient support 11 and bring one breast into the imaging volume.

Figure 3:
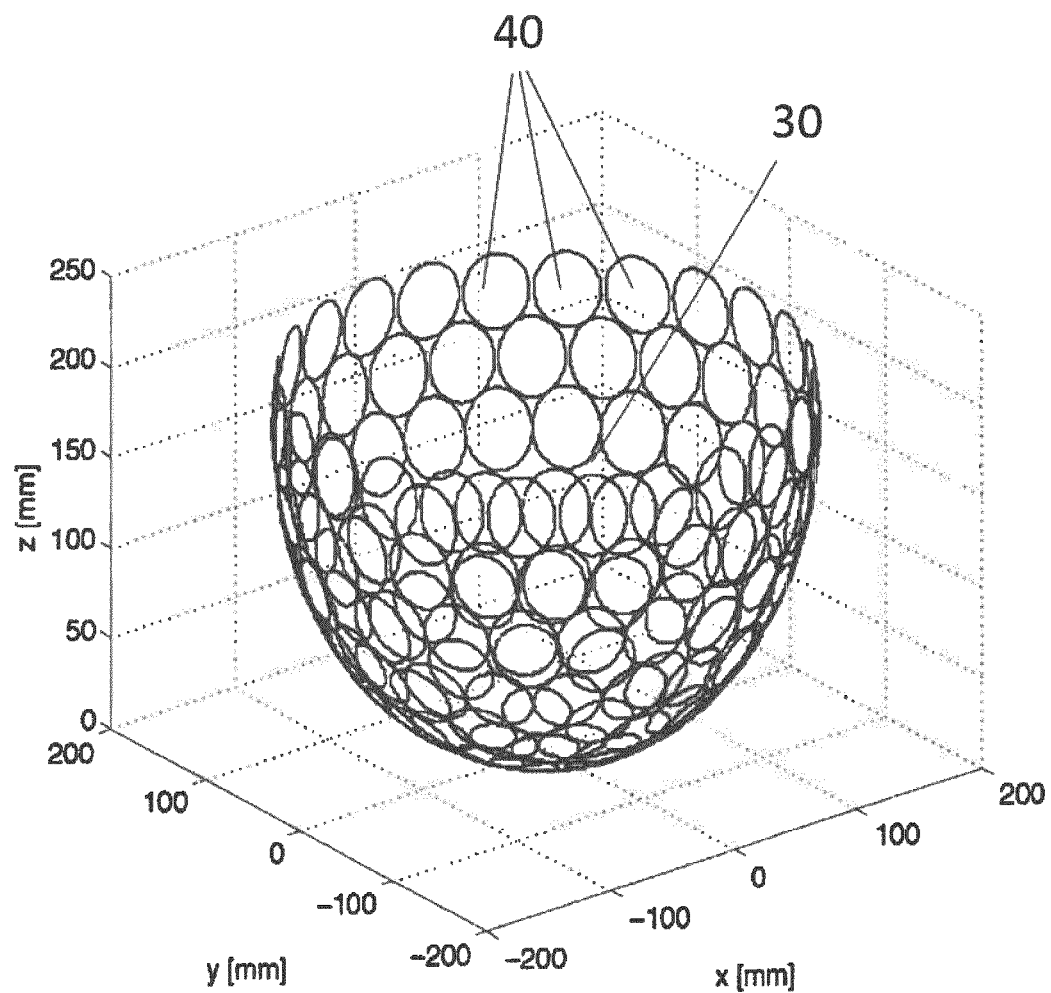
FIG. 3 shows an exemplary arrangement of a plurality of ultrasonic transducer arrays that may be held by a transducer holder.

FIG. 3 shows an exemplary arrangement of a plurality of ultrasonic transducer arrays that may be held by a transducer holder. FIG. 3 shows, by way of example, the arrangement with the highest spatial density of round transducer arrays 40 on a surface of the imaging volume 30 that has a hemispherical shape (e.g., an exemplary radius of curvature r=175 mm). Each of the transducer arrays 40 in FIG. 3 may contain a group of ultrasonic transducers, which may make the total number of ultrasonic transducers held by the transducer holder 14 to be several thousands. In other words, each of the plurality of ultrasonic transducers may be located in one of the transducer arrays 40. In the particular example of FIG. 3, each transducer array 40 is round and has a predefined identical diameter. In some cases, all the transducer arrays 40, and in particular their arrangement and number of ultrasonic transducers, may be identical, the geometric arrangement of ultrasonic transducers in the transducer arrays 40 following an aperiodically random uniform distribution. Periodicity of the transducer arrays may be prevented by randomly uniformly distributed rotation of adjacent transducer arrays.

In the exemplary embodiment, the transducer holder 14 (see e.g., FIG. 2) may define the imaging volume 30 as shown in FIG. 3. Further in the exemplary embodiment, the transducer holder 14 may hold a plurality of ultrasonic transducers in the transducer arrays 40 arranged as shown in FIG. 3. It should be noted, however, that the imaging volume defined by the transducer holder 14 may have a shape other than the hemispherical shape as shown in FIG. 3 and that the shape and/or the arrangement of the transducer arrays may be different from the shape and/or the arrangement shown in FIG. 3. For example, the imaging volume may have a spherical shape, a hemispherical shape (with a radius of curvature different from that of the example of FIG. 3), an ellipsoidal shape, a semi-ellipsoidal shape, a cylindrical shape, or any combination thereof. Further, for example, the shape of the transducer arrays may be round, ellipsoid, oval or polygonal. Further, in some examples, the transducer arrays arranged on the imaging volume may comprise fields with different shapes. The details of different examples for the shape of the imaging volume as well as the shape and arrangement of the transducer arrays may be found in EP 3107459 B1.

Figure 4:
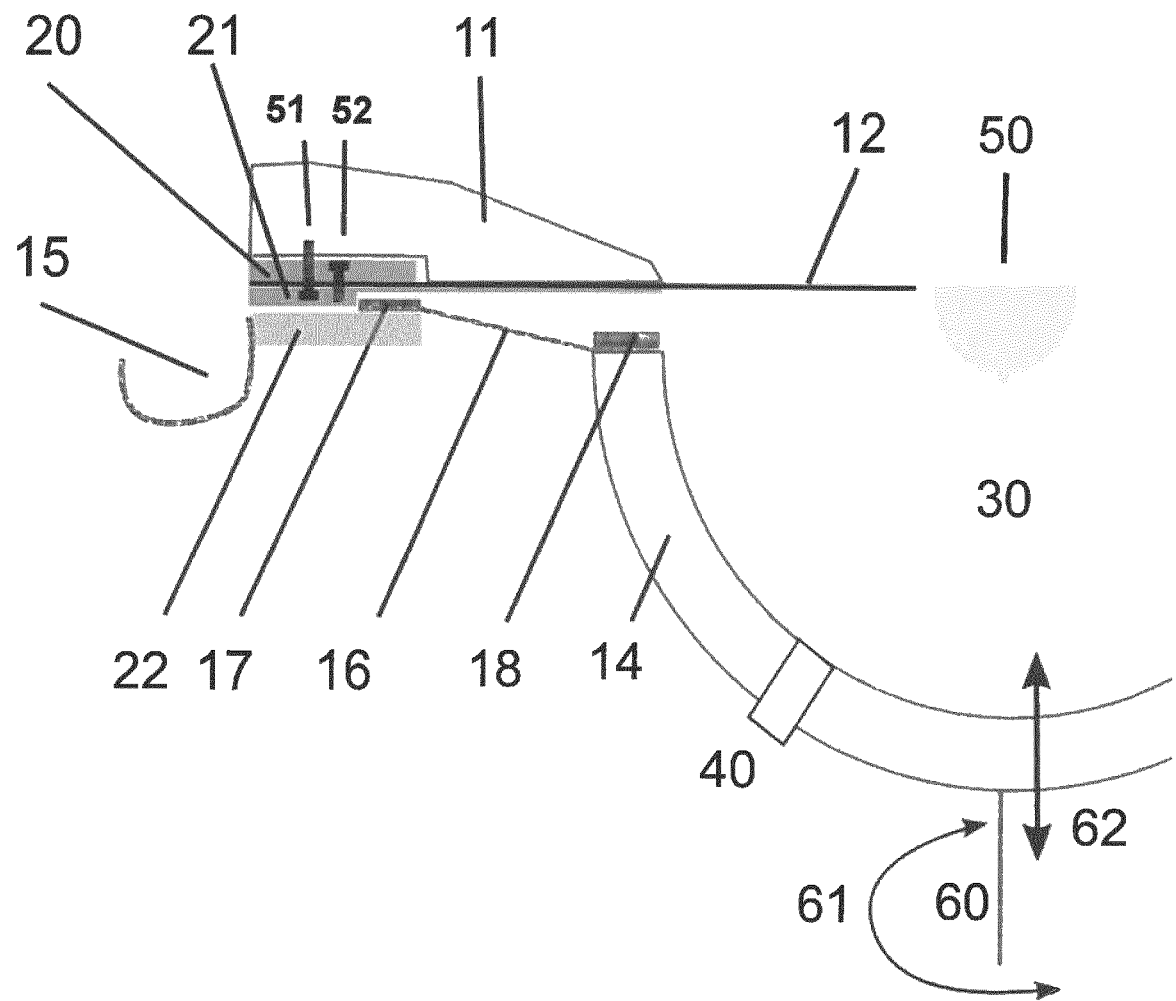
FIG. 4 shows an exemplary schematic cross section of a part of the device shown in FIG. 1.
Figure 5:
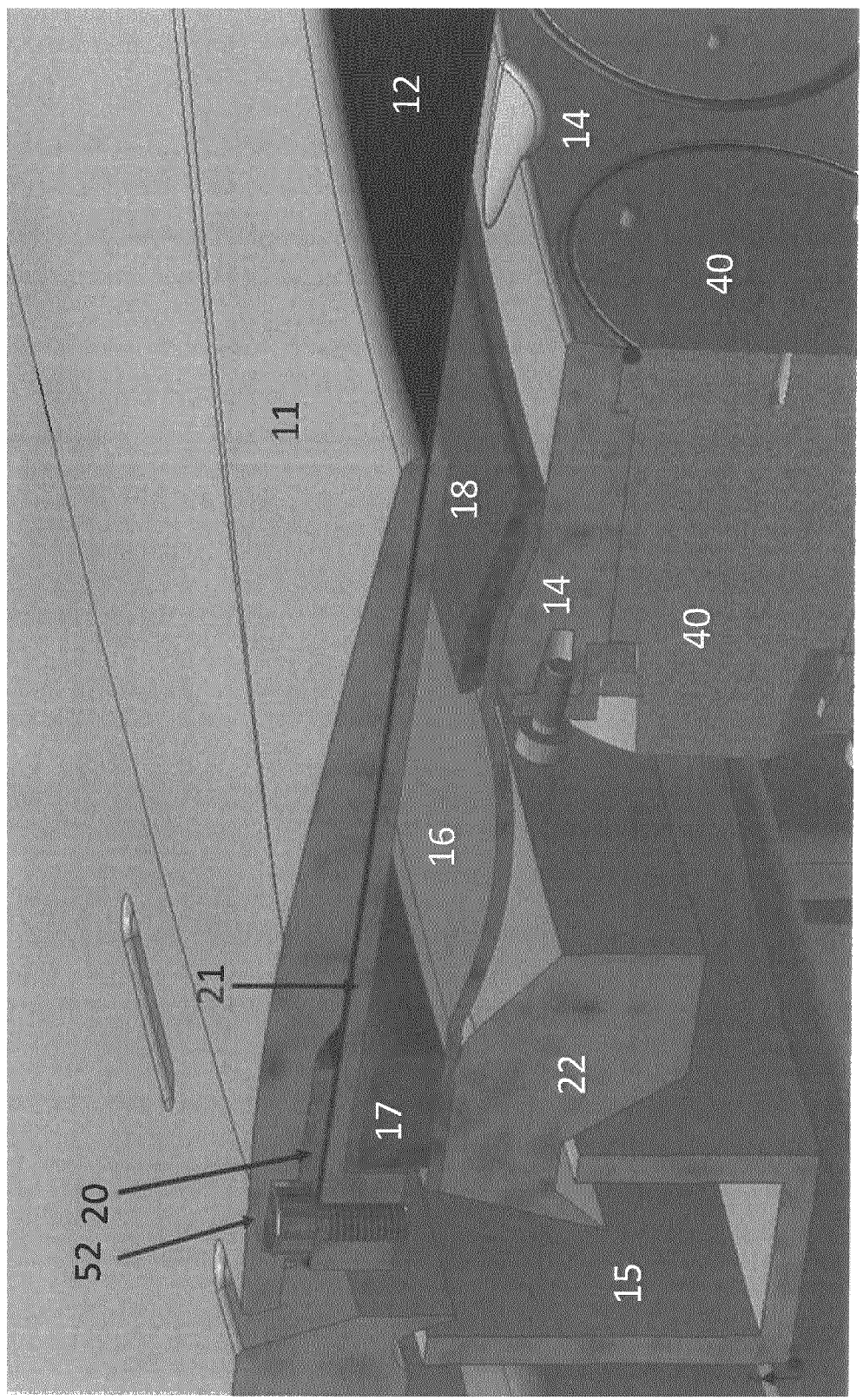
FIG. 5 shows, by way of example, a detailed, partial cross section of a part of the device shown in FIG. 1.

Details of exemplary configuration of the device 10 shown in FIG. 1 will now be described with reference to FIGS. 4 and 5. FIG. 4 shows an exemplary schematic cross section of a part of the device 10 shown in FIG. 1. FIG. 5 shows, by way of example, a detailed, partial cross section of a part of the device 10 shown in FIG. 1. FIGS. 4 and 5 show the patient support 11, the diaphragm 12, the transducer holder 14, the water outlet 15 and the elastic membrane 16. FIGS. 4 and 5 further show a top clamp ring 20 and a bottom clamp ring 21 between which the diaphragm 12 may be placed, a membrane support ring 22 as well as the mounting rings 17 and 18 for the elastic membrane 16. In the specific example shown in FIGS. 4 and 5, since the transducer holder 14, the water outlet 15, the elastic membrane 16, the mounting rings 17 and 18 as well as the membrane support ring 22 may be rotated together about a common rotation axis 60 (see FIG. 4), the diaphragm 12 and its clamp rings 20 and 21 may be at a fixed position (e.g., fixed height and no rotation) with respect to the support member 11. Further details of the diaphragm 12 and the clamp rings 20 and 21 will be described later below with reference to FIGS. 7 and 8. In the specific example shown in FIGS. 4 and 5, among the parts of the device shown in FIGS. 4 and 5, only the transducer holder 14 with elastic membrane 16 and the mounting ring 18 (for fixing the elastic membrane 16 to the transducer holder 14) are movable in a direction substantially perpendicular to the rotation axis 60 (see e.g., an arrow 62 in FIG. 4). The level of the water can be controlled by the height of the mounting ring 17 for fixing the elastic membrane to the water outlet 15.

A screw 52 may screw the top clamp ring 20, the diaphragm 12 and the bottom clamp ring 21 together so that the diaphragm 12 can be held tightly between the top clamp ring 20 and the bottom clamp ring 21, as can be seen from FIG. 4. In some other examples, the screw 52 may screw only the top clamp ring 20 and the bottom clamp ring 21 together without penetrating the diaphragm 12 but still tightly holding the diaphragm 12 between the top clamp ring 20 and the bottom clamp ring 21. Further, as can be seen from FIG. 4, a rotational block screw 51 may screw through the bottom clamp ring 21, the diaphragm 12 and the top clamp ring 20 in order to fix the top clamp ring 20 and the diaphragm 12 to the patient support 11 (as can be seen also in FIG. 8).

Further, in some exemplary embodiments, the diaphragm 12 may be glued to the bottom clamp ring 21 and both the diaphragm 12 and the bottom clamp ring 21 may be screwed together to the bottom of the patient support 11 without a top clamp ring 20.

Further, the membrane support ring 22 may be provided on an edge of the water outlet 15 and screwed to the mounting ring 17 and the elastic membrane 16, so that one side of the elastic membrane 16 can be fixed to the water outlet. The other side of the elastic membrane 16 can be fixed to the transducer holder 14 by the mounting ring 18. The details on how the elastic membrane 16 may be fixed to the transducer holder 14 and the water outlet 15 will be described later below with reference to FIGS. 6a and 6b.

Further, referring to FIG. 4, during an imaging of a breast 50, a patient (not shown) may lie on his/her stomach on the patient support 11 and insert the breast 50 into an imaging volume 30 through the diaphragm-opening 13 of the diaphragm. As described above with reference to FIGS. 2 and 3, the imaging volume 30 may be defined by the transducer holder 14 and filled with an ultrasonic coupling medium, e.g. water. The ultrasonic coupling medium displaced by inserting the breast 50 may be guided towards the water outlet 15. The mounting ring 17 may keep the water level within a desired range. In other words, the mounting ring 17 may stabilize the level of the water flowing out from the imaging volume when the at least one part of the body to be imaged is entered into the imaging volume and/or during imaging. be considered as a water level stabilizing ring. The diaphragm 12 may support the breast 50 and the chest (not shown) of the patient, while preventing other parts of the body, e.g., the second breast from entering the imaging volume 30.

Although FIG. 4 shows, as an example, one ultrasonic transducer array 40 held by the transducer holder 14, it should be understood that more than one ultrasonic transducer array (e.g. each transducer field array keeping a group of ultrasonic transducers, thereby letting the transducer holder 14 hold several thousand ultrasonic transducers) may be held by the transducer holder 14 and be used for imaging, as described above with reference to FIG. 3, for example. An ultrasonic transducer within one of the ultrasonic transducer arrays 40 may emit ultrasound waves that reach the breast 50 and/or the chest (not shown) of the patient. The ultrasound waves may reach one or more parts of the breast 50 and/or the chest that are covered by the diaphragm 12 since the diaphragm 12 may be made of an ultrasound transmissive material such as hemp, as described above. The ultrasound waves reflected at/in and/or transmitted through the breast 50 and/or the chest may be received by at least some of the plurality of ultrasonic transducers. From the received, reflected and/or transmitted ultrasound waves, images of the breast 50 (and the chest) may be reconstructed. During the imaging, the transducer holder 14 may be rotated about a rotation axis 60 in both directions as shown by an arrow 61. The rotation axis 60 may be substantially perpendicular to the opening of the transducer holder 14. Further, the transducer holder 14 may be lifted towards and/or lowered away from the patient support 11, in the directions shown by the arrow 62. The direction(s) for the transducer holder 14 to be lifted and/or lowered may be substantially parallel to the rotation axis 60.

As also stated above, in various aspects and embodiments as described herein, the transducer holder 14 (see e.g., FIGS. 2, 4, 5, 6a and 6b) holding the plurality of ultrasonic transducers may move during imaging of the at least one part of the body (e.g., human breast) to be imaged, with respect to the body to be imaged. More specifically, in some exemplary embodiments, the transducer holder 14 holding the plurality of ultrasonic transducers may be rotated and/or lifted around the suspended breast during the recording process. The elastic membrane 16 (see e.g., FIGS. 2, 4, 5, 6a and 6b) may allow the lift of the transducer holder 14 during imaging in a fluid-tight (e.g., watertight) manner. In other words, the elastic membrane 16 may allow one degree of freedom of movement (e.g., lifting) for the transducer holder 14. The axis of rotation may be, for example, substantially perpendicular to the opening of the transducer holder 14 and substantially at a center of the opening of the transducer holder 14 (see e.g., the rotation axis 60 shown in FIG. 4; the axis Z shown in FIGS. 6a and 6b). Further, the transducer holder 14 may be lifted towards the patient support 11 (and/or lowered to be away from the patient support 11) in a direction substantially perpendicular to the opening of the transducer holder 14 (see e.g., FIGS. 4, 6a and 6b). In other words, the transducer holder may be lifted (and/or lowered) in a direction substantially parallel to the axis of the rotation Z of the transducer holder 14 (see FIGS. 6a and 6b; see also, the rotation axis 60 in FIG. 4). Since the elastic membrane 16 may be a thin, soft membrane, the elastic membrane 16 may reduce motion resistance compared to a rigid cuff solution with several O-rings, which may limit the movement speed and thus the recording speed. The elastic membrane 16 can thus reduce sudden jerky movement and resulting positional inaccuracies.

As also stated above, in case imaging of the breast base is desired, the top transducers may be required to come as close as possible to the chest wall in the maximum translation of the transducer holder 14. In some exemplary embodiments, in the uppermost position of the transducer holder 14, the suspension mechanism of the elastic membrane 16 (see e.g., FIGS. 6a and 6b) may be only up to 3 mm in height. In other words, a distance from one or more upper transducers and a lower edge (e.g., an edge on a side facing the transducer holder 14) of the opening of the patient support 11 may be up to 3 mm when the transducer holder 14 is placed in a position closest to the patient support 11 during movement of the transducer holder 14 and particularly when the diaphragm 12 is sagging by the weight of the body to be imaged. For example, in case of imaging a human breast, the diaphragm 12 may sag by, e.g., about 5 mm by the weight of the patient. The one or more upper transducers may be one or more of the plurality of ultrasonic transducers that is held closest, among the plurality of ultrasonic transducers, to the opening of the transducer holder 14. Accordingly, such a suspension mechanism of the elastic membrane 16 may allow the breast base to be completely (or almost completely) imaged.

When imaging the at least one part of the body (e.g., human breast), it may be preferable that the at least one part of the body is centered in the imaging volume. Further, in case the one part of the body is of interest for imaging, it may be preferable that other parts of the body do not enter the imaging volume. The diaphragm 12 having the diaphragm-opening 13 (see e.g., FIGS. 1, 7a, 7b and 8) may facilitate centering the at least one part of the body to be imaged. Further, the diaphragm 12 may prevent penetration, into the imaging volume, of body parts other than the one part of interest for imaging. For example, in case imaging of a human breast is desired, the diaphragm 12 may prevent penetration of other parts of the body, e.g., of the second breast, into the imaging volume.

The diaphragm 12 may comprise a textile made of a material that has a higher transmissivity of ultrasound than a material of the patient support 11, as also stated above. For example, the material of the patient support 11 may be POM and a material having a higher transmissivity of ultrasound than POM may be chosen as the material of the diaphragm 12. Further, in some circumstances, the material of the diaphragm 12 may be selected such that its reflectivity and attenuation for ultrasound is minimal in order not to interfere with the imaging process. In other words, an ultrasound transmissive material may be chosen as the material of the diaphragm 12. In some exemplary embodiments, the diaphragm 12 may be made of hemp textile, as also mentioned above with reference to FIG. 1. Preferably, wet hemp may be chosen as the material of the diaphragm 12 since wet hemp has higher strength and higher ultrasound transparency at the same time as compared to other kinds of textile, for example, cotton or wool.

The bodies or parts of the bodies to be imaged may have different sizes depending on the individuals. For example, breasts with different sizes may be imaged with the device according to the exemplary embodiment. In some exemplary embodiments, the diaphragm 12 with the diaphragm-opening 13 (see e.g., FIGS. 1, 7a, 7b and 8) may be exchangeable for adapting to different sizes of the at least one part of the body to be imaged, e.g., breasts with different sizes. For instance, diaphragms 12 may have different diameters of diaphragm-openings 13. By exchanging diaphragms 12 with different diaphragm-opening diameters, breasts of different sizes may be automatically centered on the device 10.

According to the exemplary configuration as described above with reference to FIGS. 4 and 5, the patient support 11 and the diaphragm 12 can center the at least one part of the body to be imaged on the transducer holder 14. Further, the rotating and lifting mechanism can be realized with minimal distance to the diaphragm and/or the body to be imaged (e.g., the chest in case of imaging the breast).

Figure 6A:
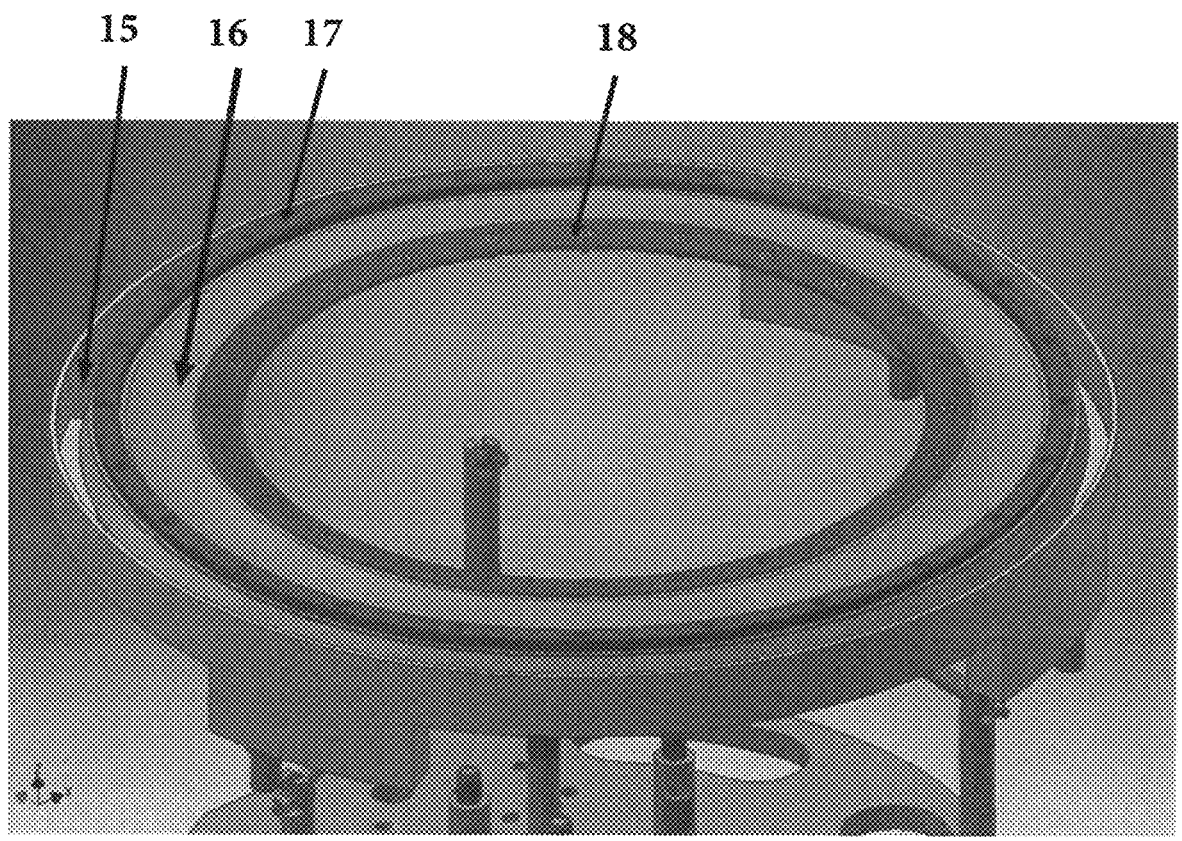
FIGS. 6a and 6b show an exemplary top view and an exemplary cut through, respectively, of an elastic membrane and fixing members fixing the elastic membrane to a transducer holder and a water outlet of the device shown in FIG. 1.
Figure 6B:
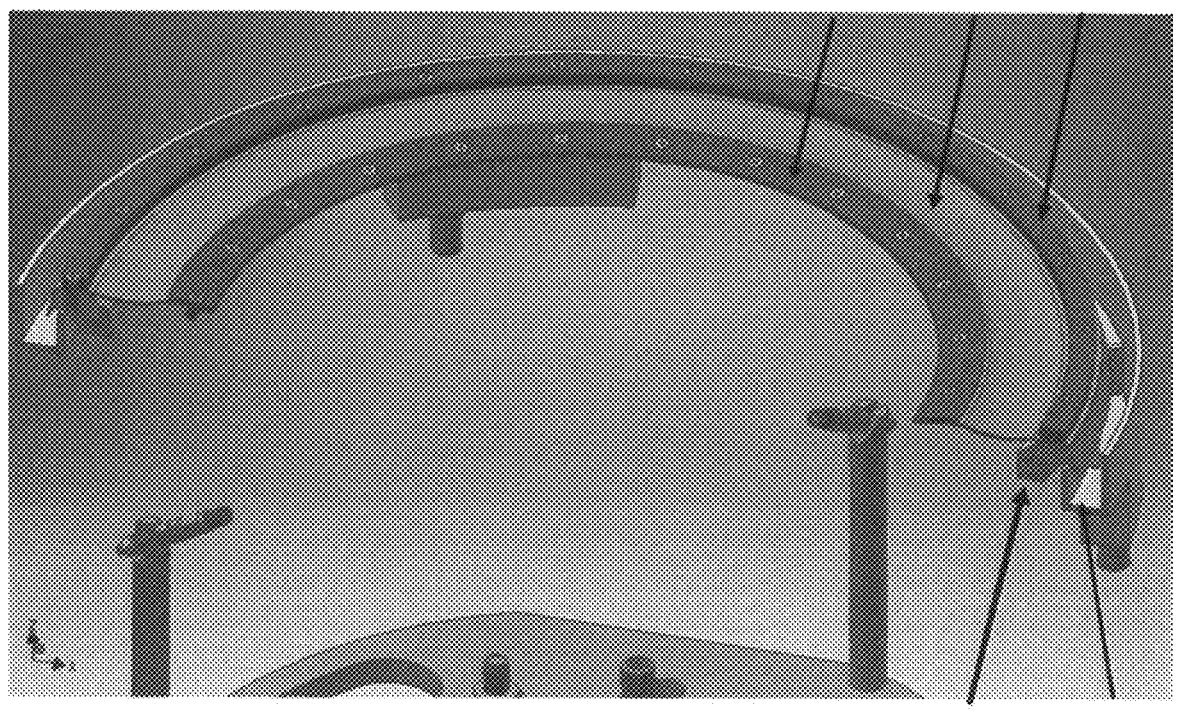

FIGS. 6a and 6b show an exemplary top view and an exemplary cut through, respectively, of the elastic membrane 16 and the mounting rings 17, 18 fixing the elastic membrane 16 to the transducer holder 14 and the water outlet of the device 10 shown in FIG. 1. FIG. 6a shows an overview and FIG. 6b shows a partial cross section of the parts shown in FIG. 6a. In the particular example shown in FIGS. 6a and 6b, the elastic membrane 16 is fixed to the support ring 22 with the mounting ring 17 (see also, e.g., FIGS. 4 and 5). Further in this particular example, the elastic membrane 16 is fixed to the transducer holder 14 with the mounting ring 18 (see also, e.g., FIGS. 2, 4 and 5).

Further, the support ring 22 may be directly connected to a rotating table (not shown) which has a constant distance to the patient support 11. On the rotating table, a device (not shown) to drive the transducer holder 14 to be lifted (and/or lowered) may also be provided. The rotating table may allow the rotation of the transducer holder 14 together with the water outlet 15, the elastic membrane, the mounting rings 17 and 18 as well as the support ring 22 around the rotation axis 60 (see e.g., FIG. 4). The rotating table may also allow, independently of the rotation, the lifting of the transducer holder 14 in the direction of 62 as shown in FIG. 4.

In some further exemplary embodiments, the elastic membrane 16 may be fixed to the transducer holder 14 and the water outlet 15 by a glue or by a screw, for example. In case the elastic membrane 16 is glued or screwed to the transducer holder 14 and the water outlet 15, the fixing rings 17 and 18 as shown in FIGS. 6a and 6b may also be additionally employed.

According to the exemplary configuration as described above with reference to FIGS. 6a and 6b, the transducer holder 14 can be lifted at a constant level of the ultrasonic coupling medium relative to the at least one part of the body suspended into the transducer holder 14 (e.g., into the imaging volume 30).

Figure 7A:
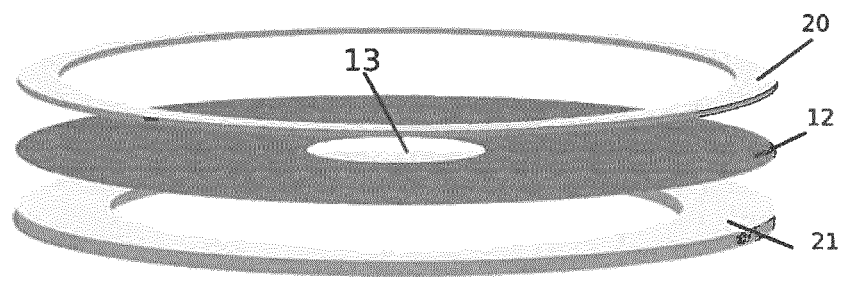
FIGS. 7a and 7b show an exemplary diaphragm and its clamp rings that may be comprised in the device shown in FIG. 1.
Figure 7B:
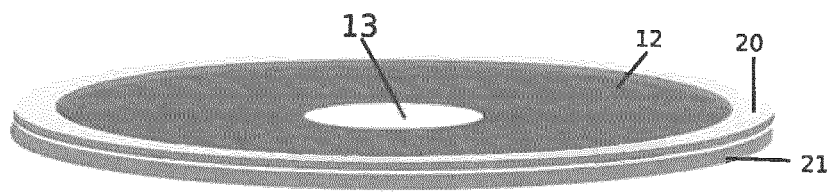

FIGS. 7a and 7b show the diaphragm 12 and the clamp rings 20 and 21 that may be comprised in the device 10 shown in FIG. 1. FIG. 7a shows an exploded view of the diaphragm 12 and the clamp rings 20 and 21 shown in FIG. 7b. It is noted that the diaphragm 12 and the clamp rings 20 and 21 are shown also in FIGS. 4 and 5.

Referring to FIGS. 7a and 7b, the diaphragm 12 may be made of hemp textile. The size of the diaphragm-opening 13 of the diaphragm 12 may be ergonomically selected for allowing the one part of the body to be imaged (e.g., human breast) to enter the imaging volume. As also stated above with reference to FIGS. 4 and 5, the top clamp ring 20 may be screwed with a bottom clamp ring 21 thereby tightly holding the diaphragm 12 between the top clamp ring 20 and the bottom clamp ring 21. It is also possible, as in the specific example shown in FIGS. 4 and 5, that screws 51 and 52 connecting the top clamp ring 20 and the bottom clamp ring 21 might additionally penetrate the diaphragm 12, thereby further holding the diaphragm 12. The bottom clamp ring 21 with the diaphragm 12 may be easily replaceable (in other words, exchangeable).

Further, in some exemplary embodiments, the diaphragm 12 may be glued to the bottom clamp ring 21 and both the diaphragm 12 and the bottom clamp ring 21 may be screwed together to the bottom of the patient support 11 without a top clamp ring 20.

Figure 8:
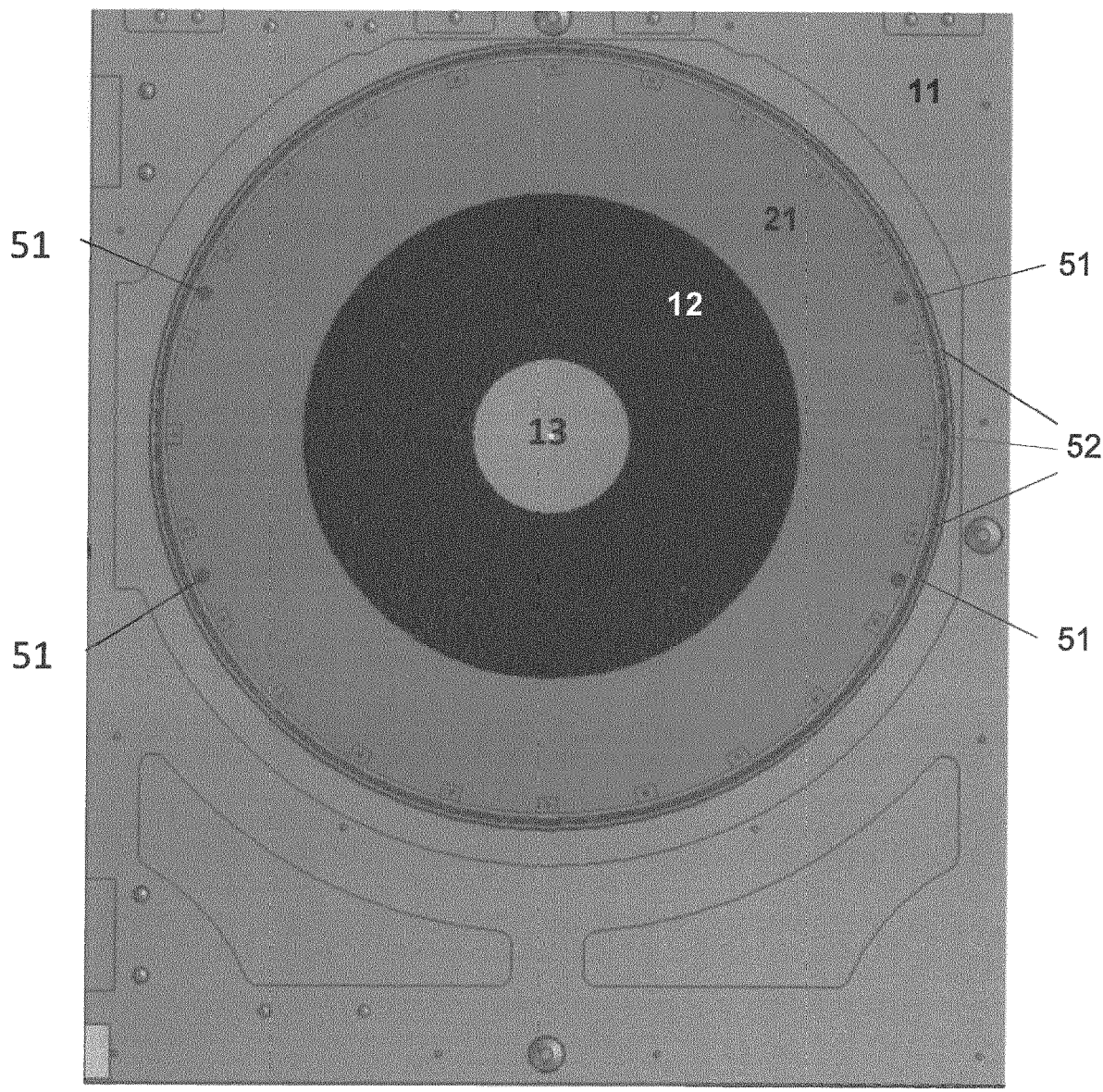
FIG. 8 shows an exemplary bottom view of a support member of the device shown in FIG. 1, with the diaphragm and the clamp rings, fixed to the support member.

FIG. 8 shows an exemplary bottom view of a support member of the device shown in FIG. 1, with the diaphragm 12 and the clamp rings 20 and 21, fixed to the support member 11. In the specific example shown in FIG. 8, the diaphragm-opening 13 in the diaphragm 12 is relatively small to adapt to smaller breast sizes. Further in the specific example shown in FIG. 8, the bottom clamp ring 21 is relatively wide to adapt to smaller bodies lying on the patient support for preventing the body to fall into the imaging volume 30. By a selection of different pre-mounted rings, the optimal adaption to the patient can be found. The screws 52 may screw the top clamp ring 20 to the bottom clamp ring 21. Further, the screws 51 may fix a packet of the top and bottom clamp rings 20 and 21 with the diaphragm 12 in between (see e.g., FIG. 7b) to the patient support 11. The number of the screws 51 (four in the specific example shown in FIG. 8) may be less than that of the screws 52.

In the exemplary embodiments described above, the diaphragm 12 is provided below the patient support 11. In other exemplary embodiments, however, the diaphragm 12 may be provided on top of the patient support 11, across the opening of the patient support 11 such that the center of the diaphragm-opening 13 of the diaphragm is placed substantially at the center of the opening of the transducer holder 14. For example, the combination of the diaphragm 12 with the top clamp ring 20 and the bottom clamp ring 21 as shown in FIGS. 7a and 7b may be screwed on top of the patient support 11, across the opening of the patient support 11. Alternatively, for example, the diaphragm 12 may be glued to the top clamp ring 20 or the bottom clamp ring 21 and both the diaphragm 12 and the top or bottom clamp ring 20 or 21 may be screwed together to the top of the patient support 11, with or without the other clamp ring 21 or 20.

Further, alternatively, for example, the patient support 11 may comprise a groove around the opening of the patient support 11 for accommodating the bottom clamp ring 21 and/or the top clamp ring 20 so that the diaphragm 12 with the top and bottom clamp rings 20, 21 may be fixed on top of the patient support 11, across the opening of the patient support 11. In this example, the diaphragm 12 held tightly between the top and bottom clamp rings 20, 21 as described above with reference to FIGS. 7a and 7b may be placed on top of the patient support 11 by fixing the top clamp ring 20 and/or the bottom clamp ring 21 in the groove. Further, for instance, the diaphragm 12 may be glued to the top clamp ring 20 and/or the bottom clamp ring 21 and placed on top of the patient support 11 by fixing the top clamp ring 20 and/or the bottom clamp ring 21 (glued to the diaphragm 12) in the groove.

Figure 9:
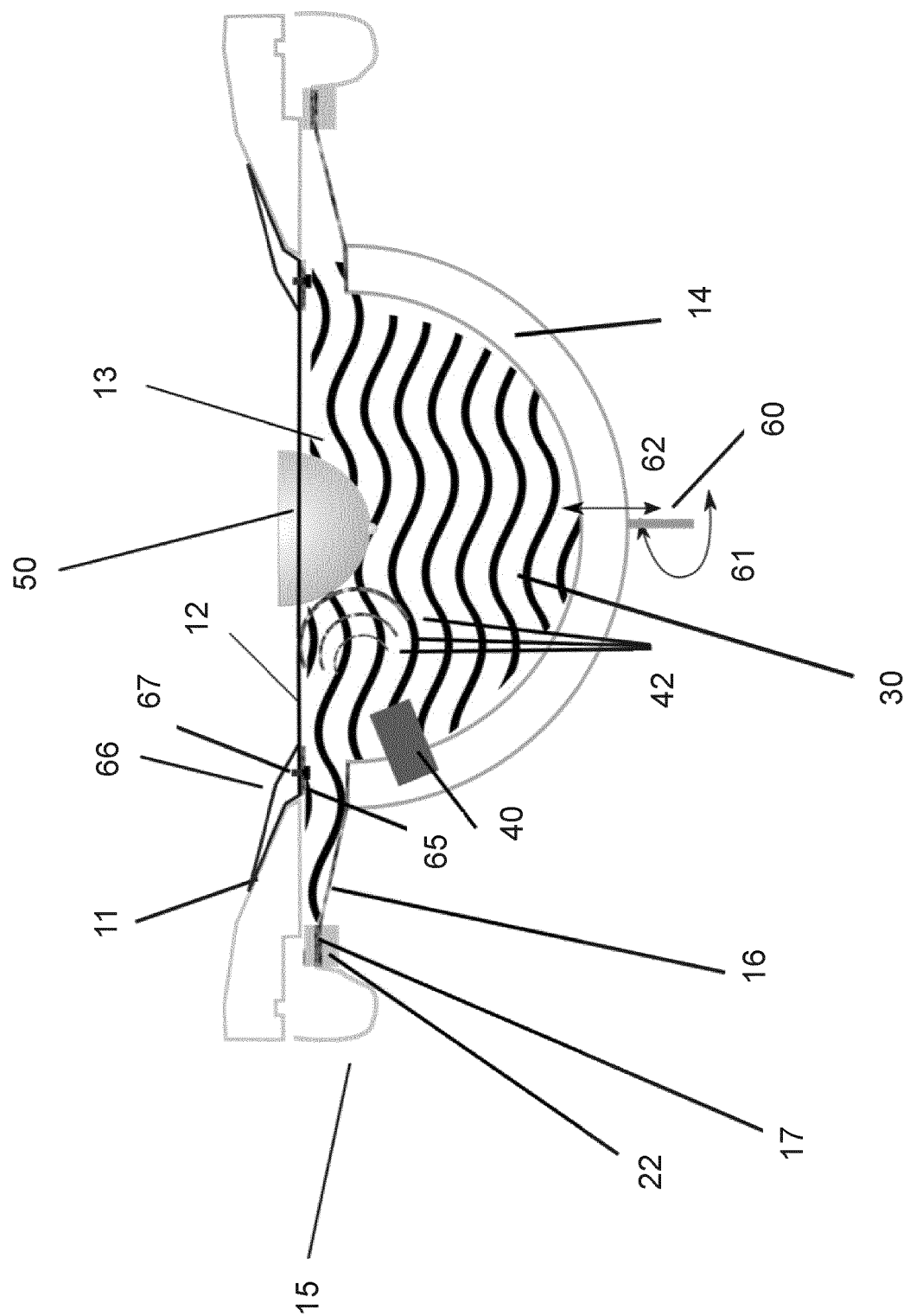
FIG. 9 shows an exemplary schematic cross section of a part of a 3D USCT device according to a further exemplary embodiment.

FIG. 9 shows an exemplary schematic cross section of a part of a 3D USCT device according to a further exemplary embodiment. In FIG. 9, elements that have the same functions as those of the device according to the exemplary embodiment as described above with reference to FIGS. 1 to 8 are shown with the same reference signs and detailed explanations on such elements will not be repeated below. In the further exemplary embodiment shown in FIG. 9, the diaphragm 12 is held tightly between a POM clamp ring 66 and a stainless-steel clamp ring 65 with screws 67. As can be seen from FIG. 9, the structure comprising the diaphragm 12, the POM clamp ring 66 and the stainless-steel clamp ring 65 may be placed on top of the patient support 11. In the particular example of FIG. 9, the POM clamp ring 66 is made of POM that may be the material of the patient support 11. Further, in the particular example of FIG. 9, the POM clamp ring 66 may have a shape such that the diaphragm 12 may be placed at the lower edge (e.g., an edge on a side facing the transducer holder 14) of the opening of the patient support 11, while the POM clamp ring 66 is supported by the patient support 11. The stainless-steel clamp ring 65 and the screws 67 may be in contact with the ultrasonic coupling medium in the imaging volume 30. In some specific examples, the stainless-steel clamp ring 65 may have a thickness of substantially 2 mm. Further, in some specific examples, the screws 67 may be M4 stainless steel screws. The number of screws 67 may be chosen as appropriate for the circumstances and, in some specific examples, may be 24.

Providing the diaphragm 12 on top of the patient support 11 may make the structure of the device simpler (e.g., manufacturing the patient support 11 may be easier and cost less) and/or may enable a faster, easier exchange of the diaphragm 12.

LIST OF REFERENCE SIGNS

10: device (e.g., 3D-USCT system)
11: patient support 11 (an example of the support member in the present disclosure)
12: diaphragm (e.g., for the vertical move of the transducer holder and/or for the support of the patient)
13: diaphragm-opening (e.g., for positioning at least one part of the body to be imaged (e.g., human breast))
14: transducer holder
15: water outlet (an example of the outlet for the ultrasonic coupling medium in the present disclosure)
16: elastic membrane (e.g., for allowing lifting of the transducer holder)
17: mounting ring (e.g., for the elastic membrane at the water outlet; this part may be considered as an example of the fixing member of the present disclosure)
18: mounting ring (e.g., for the elastic membrane at the transducer holder)
20: top clamping ring (e.g., for the diaphragm; an example of the diaphragm support in the present disclosure)
21: bottom clamping ring (e.g., for the diaphragm and support of the diaphragm up to the aperture of the patient bed; an example of the diaphragm support in the present disclosure)
22: membrane support ring (e.g., an outer mounting ring for the elastic membrane 16)
30: imaging volume (e.g., to be filled with an ultrasonic coupling medium)
40: transducer arrays (which may also be considered as a body of a transducer array containing a group of transducers)
42: ultrasonic waves
50: human breast (an example of a part of the body to be imaged)
51: rotational block screw (e.g., fixing the diaphragm 12 sandwiched between the clamping rings 20 and 21 to the patient support 11)
52: screw (e.g., fixing the bottom clamp ring 21 to the top clamp ring 20 and the diaphragm 12 in between the clamp rings 20 and 21)
60: rotation axis (which may also be a vertical axis for the lifting and/or lowering movement of the transducer holder 14)
61: rotation directions of transducer holder
62: possible vertical movement (e.g., lifting and/or lowering) of the transducer holder
65: stainless-steel clamp ring (e.g., for the diaphragm 12)
66: POM clamp ring (e.g., for the diaphragm 12)
67: screw (e.g., fixing the stainless-steel clamp ring 65 to the POM clamp ring 66 and the diaphragm 12 in between the clamp rings 65 and 66)

The invention claimed is:

1. A device for ultrasound-based reflection and transmission tomography, comprising:
a transducer holder configured to hold a plurality of ultrasonic transducers around an imaging volume to be filled with an ultrasonic coupling medium, the transducer holder having an opening for inserting, into the imaging volume, at least one part of a body to be imaged, wherein the transducer holder is configured to move, during imaging of the at least one part of the body to be imaged, with respect to the body to be imaged;
a support member configured to support, during imaging, the body to be imaged, the support member having a support-member-opening allowing access to the transducer holder by the at least one part of the body to be imaged;
a diaphragm having a diaphragm-opening, the diaphragm being arranged across the support-member-opening such that a center of the diaphragm-opening is placed substantially at a predetermined position, wherein the diaphragm comprises a material that has a higher transmissivity of ultrasound than a material of the support member;
an outlet for the ultrasonic coupling medium to flow out of the imaging volume when the least one part of the body to be imaged is inserted into the imaging volume filled with the ultrasonic coupling medium and/or during imaging; and
an elastic membrane comprising a fluid-tight material connecting the transducer holder and the outlet in order to guide the ultrasonic coupling medium flowing out of the imaging volume towards the outlet.

2. The device according to claim 1, wherein the predetermined position is a center of an opening of the transducer holder.

3. The device according to claim 1, further comprising:
a fixing member that is configured to fix the elastic membrane to the outlet and that is configured to keep, during imaging, a level of the ultrasonic coupling medium constant relative to the at least one part of the body to be imaged.

4. The device according to claim 1, wherein the diaphragm is made of the material that has the higher transmissivity of ultrasound than the material of the support member.

5. The device according to claim 1, wherein the elastic membrane is configured to allow the transducer holder to move while preventing the ultrasonic coupling medium outside the imaging volume from coming into contact with the plurality of ultrasonic transducers.

6. The device according to claim 1, wherein the transducer holder is configured to rotate, during imaging of the at least one part of the body to be imaged, with respect to the body to be imaged.

7. The device according to claim 1, wherein a distance from an upper transducer to a lower edge of the support-member-opening is up to 3 mm when the transducer holder is placed in a position closest to the support member during movement of the transducer holder and when the diaphragm sags towards the transducer holder,
wherein the upper transducer is one of the plurality of ultrasonic transducers that is held closest, among the plurality of ultrasonic transducers, to the opening of the transducer holder,
wherein the lower edge is an edge of the support-member-opening on a side facing the transducer holder, and
wherein the diaphragm may be placed at the lower edge of the support-member-opening.

8. The device according to claim 1, wherein the diaphragm is placed at a lower edge of the support-member-opening, the lower edge being an edge of the support-member-opening on a side facing the transducer holder.

9. The device according to claim 1, wherein the diaphragm is placed on top of the support member across the support-member-opening such that a center of the diaphragm-opening is placed substantially at the predetermined position.

10. The device according to claim 9, wherein the support member comprises a groove around the support-member-opening;

wherein the diaphragm is attached to at least one diaphragm support that is configured to fit in the groove; and wherein the diaphragm is placed on top of the support member across the support-member-opening by fitting the at least one diaphragm support in the groove.

11. The device according to claim 1, wherein the diaphragm is exchangeable for adapting to different sizes of the at least one part of the body to be imaged.

12. The device according to claim 1, wherein the material of the diaphragm is hemp.

13. The device according to claim 1, wherein the support-member-opening corresponds to the opening of the transducer holder, wherein the support-member-opening may be smaller than the opening of the transducer holder.

14. A method for imaging at least one part of a body with ultrasound-based reflection and transmission tomography, the method comprising:

providing the device according to claim 1;

providing the plurality of ultrasonic transducers on the transducer holder; and filling the imaging volume with the ultrasonic coupling medium;

inserting the at least one part of the body into the imaging volume; and imaging the at least one part of the body by moving the transducer holder with respect to the body to be imaged.

15. The method according to claim 14, wherein the transducer holder is rotated, during the imaging, with respect to the body to be imaged.

16. The device according to claim 1, wherein the transducer holder is configured to move, during imaging of the at least one part of the body to be imaged, in a direction substantially perpendicular to the opening of the transducer holder.

17. The method according to claim 14, wherein the transducer holder is moved, during the imaging, in a direction substantially perpendicular to the opening of transducer holder.

* * * * *